United States Patent [19]

Drobish

[11] 4,200,090
[45] Apr. 29, 1980

[54] VAGINAL CONTRACEPTIVE AND METHOD OF USING

[75] Inventor: James L. Drobish, Cincinnati, Ohio

[73] Assignee: The Procter & Gamble Company, Cincinnati, Ohio

[21] Appl. No.: 3,452

[22] Filed: Jan. 15, 1979

[51] Int. Cl.² .............................................. A61F 5/46
[52] U.S. Cl. .................................... 128/127; 128/260
[58] Field of Search ......................... 128/127, 260, 285

[56] References Cited

U.S. PATENT DOCUMENTS

| | | | |
|---|---|---|---|
| 2,097,033 | 10/1937 | McVittie | 128/127 |
| 2,423,356 | 7/1947 | Waterbury | 128/127 |
| 2,580,133 | 12/1951 | Sheen | 128/127 |
| 2,697,057 | 12/1954 | Senger et al. | 128/127 |
| 3,015,598 | 1/1962 | Jones | 128/127 |
| 3,216,422 | 11/1965 | Steiger et al. | 128/285 |
| 3,279,996 | 10/1966 | Long et al. | 167/82 |
| 3,786,807 | 1/1974 | Dubin | 128/127 |
| 3,948,254 | 4/1976 | Zaffaroni | 128/127 |
| 3,971,367 | 7/1976 | Zaffaroni | 128/260 |
| 3,983,874 | 10/1976 | Davis et al. | 128/285 |
| 3,991,760 | 11/1976 | Drobish et al. | 128/260 |
| 3,993,073 | 11/1976 | Zaffaroni | 128/130 |
| 3,995,633 | 12/1976 | Gougeon | 128/260 |
| 3,995,634 | 12/1976 | Drobish | 128/260 |
| 4,012,497 | 3/1977 | Schopflin | 128/130 |
| 4,016,251 | 4/1977 | Higuchi et al. | 128/130 |
| 4,067,961 | 1/1978 | Laughlin | 128/260 |

FOREIGN PATENT DOCUMENTS

243186 11/1925 United Kingdom ..................... 128/127

*Primary Examiner*—Lawrence W. Trapp
*Attorney, Agent, or Firm*—Jerry J. Yetter; Jack D. Schaeffer; Richard C. Witte

[57] ABSTRACT

A device which is used in the vagina to deliver spermicidal surfactants. This device can be inserted by the user, and does not require insertion by a physician as, for example, in the case of intrauterine contraceptive devices. By virtue of its unique construction and shape, the device herein is foldable for easy insertion. Once in position at the cervical os, the device opens to "cap" the os and remain in position, even during intercourse, so that access of the spermicidal surfactant source to the cervical os is not interrupted. The device is designed to remain comfortably in the vagina during the time between menstrual periods to provide desirable, prolonged release of a spermicidal surfactant, and its construction and shape facilitate retention therein while minimizing awareness and discomfort. An effective between-period contraceptive device is thereby provided.

17 Claims, 5 Drawing Figures

VAGINAL CONTRACEPTIVE AND METHOD OF USING

Technical Field

Current methods for achieving artificial contraception include the condom, the diaphram, the intrauterine device or IUD, and oral (hormonal) contraceptives. Each of these methods has disadvantages which prevent their complete acceptance either by users or by medical authorities.

Oral conceptives ("the Pill") are popular but are accompanied by the many side effects which tend to accompany any use of estrogens and/or progestins at levels which alter the hormonal balance of the body. For example, the Pill suppresses lactation. Thus, in social or cultural groups where mother's milk is a major nutrient for children up to the age of three, oral conceptives may be economically unacceptable. Other complications of oral contraceptive therapy, such as thromboembolism, can be fatal. Finally, oral contraceptives in current use must be taken according to a strict daily regimen, which means that they can only be effectively used by women who are sufficiently motivated to follow such a regimen.

The intrauterine device, or IUD, must be aseptically inserted into the uterus by a trained person, usually a physician. This involves additional time and expense to the user. Also, clinical experience over the past few years indicates that complications, including excessive bleeding, backache, spontaneous expulsion, and uterine perforation occur in approximately one-third of IUD users.

Condoms and diaphrams, while safe, fairly effective, and non-hormonal, both have the problem that they are single-use devices, and must be applied or inserted immediately prior to intercourse, presenting a social and/or aesthetic disadvantage as compared with devices which can be used unattended for long periods.

The devices of the present invention combine the desirable features of devices which provide prolonged release of medicaments, e.g., spermicides, or the like, through a membrane and into the vaginal area with the added advantages that the unique construction and shape of the present devices allow them to be worn comfortably in the vagina for periods of several weeks and to remain substantially undisturbed within the vaginal cavity during sexual intercourse. The surfactants employed as the active agent of the contraceptive devices of the present invention appear to function by an entirely localized effect on motile sperm. Accordingly, undesirable side effects which can accompany the prolonged use of systemic contraceptive drugs such as hormones are avoided.

The configuration of the present devices allows them to be positioned in close proximity to the cervical os (i.e., actually touching or within a distance of ca. 1 mm. to 10 mm), and substantially enveloping and capping the cervical os. Thus, the present devices deliver the spermicidal surfactants more efficiently and effectively than the torus shaped devices known to the art. Moreover, the configuration of the present devices provides substantial protection by virtue of the mechanical barrier the devices present to motile sperm.

While a rimless construction for the present device would yield minimal user awareness during all types of wear and, importantly, minimal awareness for both partners during intercourse, a rimmed design provides maximum position retension because the rim gives an interference fit with the cervix, i.e., it "hooks" the cervix and resists lateral movement past the cervix. The internal rim used in the present devices allows them to be fashioned in foldable, yet vaginally-retainable design which is substantially more comfortable in use than the devices disclosed by Drobish and Gougeon in U.S. application Ser. No. 748,267, filed Dec. 7, 1976, and retains its position over the cervix better than the devices disclosed by Drobish and Gougeon in U.S. application Ser. No. 840,872, filed Oct. 11, 1977.

Controlled release devices of the present type respond rapidly to changes such as dilution effects in the external environment, e.g., by body fluid changes, whereas sustained release articles do not; see Cowsar, in "Advances in Experimental Medicine and Biology", Vol. 49, *Controlled Release of Biologically Active Agents*, Tanquary and Lacey, eds., Plenum Press, New York 1974. The net result is that the present devices are capable of rapidly establishing an effective level or concentration of spermicide in a selected environment, and then substantially shutting off release to maintain the concentration at that level. In contrast, sustained release articles dispense an agent at a constant rate and do not display the feedback regulation of release that a controlled release article displays.

It will be appreciated that devices operating by the controlled release mechanism provide substantial advantages over sustained release articles for certain uses. For example, placement of a properly formulated controlled release medicament system in an animal's body cavity in contact with body fluids establishes and maintains an effective concentration of the medicament in the fluids. The system responds to dilution or depletion as additional fluids are secreted, or the medicament is bound to tissue, absorbed, etc., thereby automatically maintaining the concentration of medicament at the proper level.

As disclosed by Laughlin in U.S. Pat. No. 4,067,961 (1/10/68), solutions of micelle-forming surfactant compounds can be releasably enclosed in a container comprising a microporous membrane. Articles thus prepared are stable and do not suffer osmotic rupture when placed in body cavities in contact with body fluids. Rather, the stable articles provide controlled release of the surfactant into the body fluids. The proper selection of membrane and surfactant provides a means for achieving various biological effects, e.g., antimicrobial activity, spermicidal activity, and the like. Laughlin teaches the use of porous membranes such as cellulose. However, cellulose is fragile and is quite difficult to fashion into controlled release devices.

In the present invention various non-porous elastomers are fashioned into membranes which allow passage of spermicidal surfactant monomers therethrough in a controlled manner. Such membranes are not fragile; accordingly, stable controlled release articles with optimal shapes for providing vaginal contraceptive protection are readily made therefrom.

Moreover, the membranes used in the present devices are *substantially impervious* to liquid water as compared to cellulose. In use, the monomers of spermicidal surfactant diffuse through the membrane into the vagina (presumably by virtue of their solubility in the membrane), whereas the surfactant micelles do not. Since the membranes are non-porous and are *substantially impervious* to bulk water and body fluids, they do not undesirably develop an internal pressure in an aqueous environment.

In contrast, osmotic pressure causes some rigidity in the devices of Laughlin, which can aid in their retention in the vagina. However, development of internal hydrostatic pressure due to osmotic effects can cause at least two disadvantages in the Laughlin devices: (1) this pressure stresses the membrane structural components of the device making them more prone to rupture under the influence of less external force than they would be otherwise; and (2) this pressure precludes the use of products having relatively broad unsupported membrane areas in the present vaginal contraceptive application. Products so designed would undesirably inflate to uncomfortable and potentially contraceptively ineffective shapes. In any case, osmotic pressure is not, per se, the force which moves surfactant out of either the Laughlin devices or the devices disclosed herein and they are thus entirely different from that of art-disclosed, osmotically-actuated "pump" devices for delivering drugs. Rather, in both cases, it is the trans-membrane chemical potential (i.e., substantially the surfactant monomer concentration) difference which causes release of spermicidal surfactant monomers from the device. However, as noted above, Laughlin employs microporous membranes, such as swollen cellulose, which contain microscopic, water-filled channels through which the monomers are transported. In contrast, the present devices use non-porous membrane materials through which the surfactant monomers migrate by first dissolving therein and then diffusing therethrough.

Moreover, the devices herein do not operate by an osmotic pressure mechanism and are thus entirely different from that of art-disclosed, osmotically-actuated "pump" devices for delivering drugs.

Highly preferred devices are those operating by a controlled release mechanism. However, devices operating by a sustained release mechanism can also be constructed in the manner disclosed herein so that they can be retained in the vagina during intercourse. Accordingly, sustained release devices of the unique construction and shape of the devices herein are fully contemplated by this invention.

Background Art

Numerous devices for contraception and/or drug delivery in the vagina have been developed. Dome-shaped diaphragms and methods for making them are described by Fickert, et al., Gr. Brit. Pat. No. 21,588; Senger, et al., U.S. Pat. No. 2,697,057; and Jones, U.S. Pat. No. 3,019,598.

The use of silicone materials to form sustained release drug delivery devices for use in the vagina is well known. The following U.S. patents disclose typical devices and formulations: U.S. Pat. No. 4,012,497, Schopflin, Silicone Drug Excipient; U.S. Pat. No. 3,971,367, Zaffaroni, Intrauterine Device Having Means for Changing from Uterine Retentive Shape to Non-Uterine Retentive Shape; U.S. Pat. No. 3,993,073, Zaffaroni, Drug Delivery Device.

The use of rate-limiting barriers in vaginal drug delivery is described in U.S. Pat. No. 4,016,251, Higuchi, et al., Vaginal Drug Dispensing Device.

As disclosed by Laughlin in U.S. Pat. No. 4,067,961, solutions of micelle-forming surfactant compounds can be releasably enclosed in a container comprising a microporous membrane, such as cellulose.

A variety of beaded torus configurations are disclosed in Gougeon and Drobish, U.S. Pat. Nos. 3,991,760 (Nov. 16, 1976) Vaginal Medicament Dispensing Means; 3,995,633 (Dec. 7, 1976) Vaginal Medicament Dispensing Device; and 3,995,634 (Dec. 7, 1976) Vaginal Cavity Dispensing Means and Method.

Externally rimmed devices are disclosed by Drobish and Gougeon in U.S. application Ser. No. 748,267, filed Dec. 7, 1976.

Rimless devices with reinforced backs are described in Drobish and Gougeon in U.S. application Ser. No. 840,872, filed Oct. 10, 1977.

DESCRIPTION OF THE DRAWINGS

FIG. 1 is an exploded perspective view of a preferred device of the present type. The halves of the device comprise two flattened, or dome-shaped, or dish-shaped discs which are assembled into an internally rimmed, externally rimless structure which provides a container for the spermicidal ingredient.

In the device of FIG. 1, the front face 11 comprises a membrane which is permeable to surfactant monomers but which is not permeable to the passage of surfactant micelles therethrough.

The back half 12 of the preferred device comprises a flexible, toxicologically-acceptable material. The material used to fashion this outer portion of the device is not critical and need not be a semipermeable membrane material.

FIG. 1 depicts a front face 11 and a back 12 of the device in proper juxtaposition for assembly. To assemble the device, the thickened edges can be sealed in any suitable fashion, such as polymer welding or adhesive sealing, thereby forming an internal rim in the assembled device depicted in perspective view as FIG. 2.

FIG. 2 is a perspective view of the assembled device of FIG. 1.

The device of FIG. 3, comprising a container formed by joining the two halves of the device, is depicted as being substantially filled with an aqueous solution of spermicidal surfactant 17. The device of FIG. 3 is depicted with the back wall 12 being somewhat thicker than the front face. This connotes, in the preferred device herein, a back wall which is less permeable to transport of surfactant than the front face. This difference in permeability serves to direct surfactant monomers preferentially through the membrane, which which is placed in proximity to the cervical os. In addition the thicker back provides extra structural support for the device, further enhancing retention.

In use, the devices herein are folded and inserted into the vagina posterior to the introitus. Once inserted, the internal rim causes the devices to open and to substantially block or cap the cervical os such that semipermeable membrane 11 is in the closest possible proximity to the os. Placement of the semipermeable membrane adjacent to the cervical os causes the os to be bathed in the spermicidal surfactant as the monomers thereof are released through the surfactant transport surface which comprises membrane 11. The internal rim 13 provides good vaginal retention by giving an interference fit with the cervix, i.e., it essentially "hooks", and is retained by its internal rim, thereby capping the cervix, to present a mechanical barrier to motile sperm.

Disclosure of the Invention

The contraceptive devices of this invention make use of the association colloid nature of solutions of certain spermicidal surfactants to provide a reservoir from which spermicide is released in a controlled manner through the semi-permeable membrane which comprises at least a portion of the front face of the device. Surfactant micelles cannot diffuse through the semi-permeable membrane as is; they must first dissociate, at or remote from the membrane, to form surfactant monomer molecules which then dissolve in the membrane material and diffuse therethrough to its outer surface, whereupon the surfactant monomers are free to dissolve in the surrounding vaginal fluid to provide their contraceptive effect. Since the predominant driving force for diffusion is the concentration difference between unassociated (i.e., substantially monomeric) surfactant molecules in the solution inside and outside the contraceptive device, the rate of transport will slow drastically when the exterior surfactant monomer concentration approaches that on the interior of the device, thus producing a desirable controlled release of the surfactant through the membrane. In the present devices, the bulk of the surfactant remains in micellar form, where it resides in reserve within the device to provide a source of monomers over a long period of time, thereby delivering continuous contraceptive protection to the user for a time period of 20–30 days.

As will be seen from the following, the present invention encompasses contraceptive devices which are especially adapted for use within the vaginal cavity at a position posterior to the introitus and in close proximity to the cervical os, characterized by: thin, flexible, comfortable walls comprising a substantially non-porous, semi-permeable membrane, one or more of said walls comprising a transport surface facing the cervical os, thereby providing a transport surface on the face of the device, said walls forming one or more containers, said containers holding a reservoir of spermicide comprising an aqueous solution of a micelle-forming spermicidal surfactant compound at a concentration at or above the critical micelle concentration of said surfactant compound, said devices being characterized by a resilient material around the interior of one or more of said walls and adjacent to the perimeter of the front face, forming an internal rim, whereby said devices are maintained in position in the vagina. Preferred devices are those wherein the transport surface extends substantially across the face of the device. Domed or "cup-shaped" devices which can be positioned to substantially block or cap the cervical os are an especially preferred embodiment of the invention.

Devices according to this invention wherein the container walls which face the cervical os comprise the only substantially non-porous, semi-permeable membrane transport surface in the device are preferred for use as contraceptives, inasmuch as the spermicidal surfactant is thereby delivered directly to its prime situs of action. Moreover, delivery of excess surfactant to the general vaginal cavity is thereby avoided. However, devices wherein all container walls comprise the substantially non-porous, semi-permeable membrane transport surface are also useful and are encompassed by this invention.

This invention also provides a method for achieving contraception in the vagina, comprising: folding and inserting within the vaginal cavity at a position posterior to the introitus and in close proximity to the cervical os, and preferably capping the os, an internally rimmed device of the foregoing type, whereupon the substantially thicker internal rim causes the device to open to present a semi-permeable membrane transport surface across, and in the closest possible proximity to, the cervical os. Surfactant monomers diffuse from the device through the membrane transport surface and substantially bathe the cervical os with surfactant in the vaginal fluids to provide a spermicidal effect on sperm coming in contact therewith.

The devices herein are prepared from components which are described in detail hereinafter.

The configuration of the devices herein is designed to provide a semi-permeable membrane as a transport surface for the surfactant monomers, said transport surface extending across the entire surface of the cervix (i.e., substantially covering the cervical os). This eliminates problems occasioned by small lateral movements of the device associated with muscular contractions/exertions of the user during wear. Most importantly, by providing a transport surface which is in the closest possible proximity to the cervix, the surfactant has the shortest possible path to the cervical os. Since conception normally requires transmittal of sperm into the os, it will be appreciated that, by delivering surfactant monomers in the most efficient manner to this point in the vagina, the most efficient and effective contraceptive protection is provided.

Container

Broadly, the present devices comprise a container, or multiple containers, said container being insoluble in vaginal fluids, in a total device of the configuration described hereinabove. The container has the surfactant solution enclosed therein. At least one portion of the container comprises a non-porous polymeric semi-permeable membrane which permits the release of surfactant monomers into the vagina, but which substantially prevents the transport of the larger surfactant micelles. In short, the membrane is the transport surface which selectively discriminates between passage of monomers and micelles.

Containers used in the present devices can be partly made of any stable material such as glass, plastic, etc., which is not permeable, even to surfactant monomers. Of course, the containers should be made from a material which is inert to the surfactant solutions being used, as well as to the vaginal tissues, but selection of inert container materials is not a problem. At least some portion of the container used in the present devices must comprise a non-microporous polymeric semi-permeable membrane which allows diffusion of the spermicidal surfactant monomers therethrough and into the vaginal cavity. For the reasons disclosed above, at least that wall of the container which faces the cervical os comprises the controlled release membrane. Alternatively, the entire device can be made of the membrane material.

Preferred controlled release devices are those wherein at least a portion of the container wall is a dish- or dome-shaped envelope of the controlled release membrane.

The semi-permeable membranes used in the controlled release devices are characterized by parameters which reflect their strength, integrity and ability to pass surfactant monomers and to retain surfactant micelles, as follows.

The membranes should be substantially water-insoluble so that they maintain their strength and integrity when in contact with body fluids.

Since the devices are to be used in contact with body fluids and tissues, the membranes (and total container and device) should be toxicologically acceptable. Moreover, the membrane material will most preferably be immunologically acceptable and will not be rejected by the body's natural defense mechanisms nor have any untoward effect on the rate of antibody formation, and the like.

The membrane must possess the ability to provide metered release of the surfactant monomers in order to provide the prolonged contraceptive benefit of the article.

The membrane must be sufficiently strong and made of a material that can be fashioned into the highly preferred shape of the devices disclosed herein.

The semi-permeable membranes employed herein comprise non-porous elastomers, preferably silicone polymers or latex rubbers, either natural or synthetic. The membranes generally have a thickness in the range from about 0.02 mm to about 0.8 mm, preferably about 0.4 mm. By selecting a membrane thickness within this range, stable, non-fragile, yet flexible and comfortable articles which effectively transport surfactant monomers to the vagina are provided.

The silicone polymers used in preparing the membranes for use in the present devices are preferably poly-dimethylsiloxanes, i.e., silicone polymers which contain the repeating unit wherein y is an integer in the range of about 100–100,000.

Repeating units of the silicone polymer can contain side-chain branching and cross-linking, e.g., Various functional groups may be present in the basic silicone polymer structure to facilitate cross-linking/curing.

Silicone polymers suitable for use herein can be prepared, for example, by hydrolyzing dimethyldichlorosilane or mixtures of dimethyldichlorosilane, trichloromethylsilane and chlorotrimethylsilane with water, in well-known fashion. Alternatively, siloxane "oligomers" can be polymerized and "cured" in various ways well known in the art. Silicone polymers suitable for preparing the membranes for use in the present invention are also available, commercially, from suppliers such as the Dow Corning Corporation and the General Electric Corporation.

The latex rubbers which can be used in the present invention can be either the natural or synthetic latex rubber polymers which are commercially available. Such materials include, for example, the neoprene-type rubbers, the Buna ®-type rubbers, and the like. Natural or synthetic rubber which is calendered or molded can also be used.

Other types of non-porous polymers which can be used to fashion membranes for use with devices of the present type comprise, for example, mixtures of silicone polymers and latex rubbers; copolymers of silicone polymers and various other polymeric materials such as the polycarbonates, and the like; elastomers such as the well-known styrene/butadiene block copolymers; ethylene-vinyl acetate copolymers, etc.

Various polymeric membranes suitable for use in the contraceptive devices of the present invention can be determined easily using the Surfactant Transport Procedure, disclosed hereinafter.

Highly preferred membranes for use herein are the non-porous membranes comprising silicone polymers, especially the polydimethylsiloxanes manufactured under "clean" conditions and marketed for various medical uses. Such materials are safe for prolonged use in contact with human tissues and provide excellent transport of surfactant monomers, especially the preferred, nonionic spermicidal surfactants of the type $C_{10}EO_5$ and $C_{10}EO_6$, as described hereinafter. These silicone polymers can readily be fashioned into membranes for use in devices having the preferred dome-shaped configuration disclosed herein. Typical examples of such silicone materials include Silastic ® 382 and Dow Corning ® MDX 4-4210 MDX 4-4515, MDX 4-4516, Q7-2213, Q7-2245, and X7-2177 available from the Dow Corning Corporation.

Spermicidal Surfactant

The use of micelle-forming surfactant solutions in the present contraceptives devices results in several important advantages over other types of metered dosage systems.

First, the surfactants employed as the active agent of the contraceptive devices of the present invention appear to function by an entirely localized effect on motile sperm. (The terms "spermicide" and "spermicidal" as employed herein encompass surfactants which truly "kill" animal, including human, sperm as well as those which immobilize or otherwise render sperm cells inactive.) Accordingly, undesirable side-effects which can accompany the prolonged use of systemic contraceptive drugs such as hormones are avoided.

Moreover, the use of safe, effective surfactants as the spermicide permits the formulator of the present devices to employ a large excess of the spermicide therewith. The controlled release feature allows formulation of devices containing more spermicide (surfactant) than the usual expected need for an extended wear period, but (1) reduces the probability of side-effects by regulating the concentration produced in the vaginal fluids to a minimum level, and (2) allows for unusual variations in the amount of spermicide required or in the time period over which it might be needed. Accordingly, a "safety factor" of the order of several-fold vis-a-vis prolonged contraceptive efficacy is provided by the present devices.

The devices herein can be somewhat flaccid, rather than turgid. Accordingly, the pressure differential across the enclosing container is small, or zero, and the container is stable and is not subject to hydrostatic rupture. This desirable attribute of the present devices is to be contrasted with the situation which occurs when a similarly concentrated solution of a non-micelle-forming solute of similar molecular weight is enclosed by a water-permeable diffusion membrane, whereupon internal hydrostatic pressures of tens or hundreds of atmospheres can be developed due to osmotic effects, thereby leading to rupture of the membrane.

The surfactants employed in the present devices and processes are characterized by several parameters. In general, the surfactants are selected from those which, in combination with the semi-permeable membrane described hereinabove, provide an appropriate relationship between release and the desired contraceptive end use of the devices.

The surfactants herein are characterized by their ability to dissolve in a solvent (normally water) and to form an association colloid, or micelles, therein. It has now been discovered that the surfactant micelles do not penetrate the walls of the membranous containers used herein. However, surfactant monomers do diffuse through the membranous walls and into the vagina. Thus, by virtue of the equilibrium between micellar and monomeric surfactant, the solution of surfactant micelles provides a reservoir for the controlled delivery of spermicidal surfactant monomers to the environment external to the device, i.e., the vagina, especially the area immediately around the cervical os. In a surfactant solution which is sufficiently concentrated to form true micelles, the concentration of monomer in equilibrium with the micellar surfactant remains substantially constant at the so-called "critical micelle concentration" (cmc) over a wide range of total surfactant concentration. In order to realize fully the unique advantages of surfactants in devices of the present type, it is preferred to use those spermicidal surfactants having a cmc of at most about $5 \times 10^{-3}$ Molar (M). In particular, by choosing surfactants with this low cmc, the user of the present devices is exposed to only minimum amounts of surfactant, thereby minimizing any possible toxicological hazards.

It is to be appreciated that "neat" surfactants, i.e., surfactants not in solution, are not in the form of micellar aggregates and, accordingly, simply pass through the walls of the membranes in an undesirable, uncontrolled manner, thereby eliminating the reservoir effect provided by surfactant micelles.

When used as between-period contraceptives, it is, of course, necessary to select surfactant which produce the desired spermicidal response. Moreover, to secure the benefits of controlled release, it is necessary also to select surfactants whose monomers are rapidly transported through the membranous walls of the container to establish an effective concentration of surfactant in the vaginal area.

From the foregoing considerations it will be appreciated that various surfactants can be tested in vitro in a simple medium which approximates various body fluids (such as physiological saline or distilled water) to determine the concentration at which the surfactant must be present in such medium to provide spermicidal efficacy. Surfactants whose monomers are transported through the enclosing membrane of the device to provide at least the aforesaid effective concentration in the medium are useful herein. Upon immersion in an external solvent (e.g., vaginal fluids) the controlled release devices herein deliver surfactant monomers to the external solvent in the rapid, or "primary", transport process. After this external concentration reaches approximately the cmc of the surfactant, monomer transport slows drastically, since monomer concentration on both sides of the semi-permeable membrane is nearly equal. Slower, "secondary" transport processes may carry a bit more of the surfactant through the membrane to the vagina, but this does not substantially deplete the surfactant reservoir in the present devices.

From the foregoing, it follows that, for the desired spermicidal effect to be realized, the ratio, R, of the cmc of the surfactant to its spermicidally-effective concentration, $C_{sperm.}$, e.g., in saline, i.e., $$R = \frac{cmc}{C_{sperm.}}$$

should be treater than or equal to about 1. Similar considerations hold for external media other than saline, i.e., fluid media such as vaginal fluids, water, etc., in which the present surfactant monomers are soluble. Accordingly, the preferred compounds for use in the devices described herein have values of R which are greater than or equal to ca. 1, i.e., $$R \geq \text{ca. } 1.$$

A variety of surfactants exhibit a cmc less than about $5 \times 10^{-3}$ M and meet this criteria for use in the preferred controlled release devices herein. Several surfactant types having this preferred cmc provide a desirable spermicidal response. Moreover, several surfactants exhibit the requisite relationship, $R \geq \text{ca. } 1$, between cmc and spermicidal activity.

Based solely on the foregoing considerations, representative examples of surfactants useful herein include nonionic surfactants such as n-$C_{10}H_{21}(OCH_2CH_2)_5OH$ (abb. $C_{10}EO_5$) and n-$C_{10}H_{21}(OCH_2CH_2)_6OH$ ($C_{10}EO_6$); semipolar surfactants such as $C_{12}H_{25}S(NH)_2CH_3$ and $C_{12}H_{25}(CH_3)_2AsO$; and cationic surfactants such as $C_{16}H_{33}N^+(CH_3)_3,Cl^-$ and $C_{16}H_{33}N^+C_5H_5,Cl^-$. These surfactants are characterized by $R \geq 2$ and cmc $< 10^{-3}$ M.

It is to be understood that other surfactants having a cmc of about $10^{-3}$ M, or less, but which exhibit somewhat lower activity as spermicidal agents, i.e., surfactants wherein ca. $1 > R < 2$, can be employed in controlled release articles. However, the biological response to these latter surfactants is somewhat less than that of the preferred group, and the efficacy margin, i.e., R-1, is not as great. Included among this group of surfactants are n-$C_{12}EO_9$; n-$C_{16}EO_1SO_4^-$,Na$^+$; $C_{12}H_{25}(CH_3)_2PO$; n-$C_{10}EO_4$; $C_{12}H_{25}(C_2H_5)_2PO$; $C_{16}H_{33}$ammoniopropanesulfonate; and nonylphenol nonaethoxylate.

As can be seen from the foregoing, various surfactant types are useful in controlled release contraceptive devices of the present type. However, when devices designed for use as between-period contraceptives in humans are being prepared, additional physio-chemical properties of the surfactants must be considered. For example, the surfactants should be toxicologically acceptable for use in the body over extended time periods. The surfactants should also be non-irritating to the delicate tissues of the vagina and uterus. The preferred surfactants should not excessively bind serum proteins found in the vaginal area between periods of menstrual flow, inasmuch as the bound surfactant-protein moiety does not function as a spermicide and binding accelerates the depletion of surfactant from the reservoir (micelles) within the device. The surfactant monomers must be able to dissolve or partition into the enclosing membrane of the device and diffuse through the membrane in an efficient and effective manner. Finally, the surfactant should be selected from those which do not bind to charged sites in the enclosing diffusion membrane, since binding inhibits the passage of the surfactant monomers through the membrane. In particular, ionic surfactants are troublesome in this regard. Moreover, some ionic surfactants are too polar to partition into and diffuse through the preferred silicone membranes efficiently.

Based on the foregoing factors, and considering the high spermicidal activity of the compounds, the alkylene oxide nonionic surfactants, especially the well-known condensation products of ethylene oxide with aliphatic alcohols or alkyl phenols, are preferred for use herein. In particular, $C_{10}EO_5$ and $C_{10}EO_6$ surfactants are most preferred for use in the present controlled release contraceptive devices. As between these latter compounds, $C_{10}EO_5$ has the advantage of the lower molecular weight, and therefore provides more spermicidal monomer per given weight of compound. Accordingly, $C_{10}EO_5$ is most preferred for use in the between-period, controlled release contraceptive devices of this invention.

The surfactants disclosed hereinabove are all well known from the detergency arts and can be made by various art-disclosed processes.

Surfactant Transport Procedure

A cell for testing transport of surfactant monomers through membranes is as follows. A 40 mm (diameter)×50 mm (length) stainless steel rod is halved and each half is suitably machined to provide cavities 16 mm (diameter)×10 mm (depth), such that the cavities abut when the rod halves are reassembled. Each cavity is provided with two inlet holes for filling and sampling. A brass clamp is used to hold the two cell halves firmly together.

The surfactant transport testing is carried out in the following manner. A disc 3 cm. in diameter of the membrane material to be tested is sandwiched between the cell halves, enclosing a 3 mm glass bead on each side of the membrane to provide stirring. One half of the cell is filled with distilled water and the other half is filled with an aqueous solution of a radiolabeled surfactant. The inlet holes are sealed with waterproof tape and the cell is placed in a 37° C. bath in a device which allows the cell to be rotated axially at approximately 50 rpm. Periodically, the cell is raised from the bath and the solution in the desired compartment sampled.

A typical procedure using a membrane of polydimethyl-siloxane (Dow Corning ® MDX 4-4210) is as follows. After charging the cell, the cell is maintained in the 37° C. bath for varying time periods, after each of which the tape is removed from the inlet holes and duplicate 10 microliter (μl) samples are removed by syringe and expressed into a counting vial. In the subsequent scintillation counting, each sample vial is charged with 10 μl of a solution of 0.8% 2-diphenyloxazole and 0.01% of 1,4-bis-[2-(4-methyl-5-phenyloxazolyl)]-benzene in a 1:1 ethanol/toluene mixture. The vials (two for each time period) are then placed in the refrigerator compartment of a counting instrument and cooled to 4° C. before being counted for 5 minutes each. The counts per minute are converted to ppm by applying a factor found by counting one or more standard samples. By taking samples at regular intervals, a curve plotting the surfactant concentration in the initially surfactant-free side of the cell versus the time of sampling can be drawn which describes the transport of the surfactant across the membrane.

Following the Surfactant Transport Procedure set forth hereinabove, the cell cavity designated (A) is charged with surfactant solution and the cavity designated (B) is charged with distilled water. The cell cavities are separated by the test membrane, e.g., polydimethylsiloxane. The concentration of surfactant transported by cavity (B) is determined in the foregoing manner, and the graph of the concentration of surfactant in (B) versus time is plotted.

This graph describes a monomer transport curve which at the outset rises at a high rate (primary slope) and beyond a certain time rises at a much lower rate (secondary slope). The monomer transport curve has the general form $C=C_2(1-e^{-t/\pi})+S_2t$, where C=surfactant concentration in cavity (B), $C_2$=the zero time intercept of the secondary slope, t=time, $\pi$=the time constant, and $S_2$=the secondary slope. The primary slope, $S_1$, is the slope of the curve at t=0 and is given by $$S_1 = \frac{C_2}{\tau} + S_2.$$

For controlled release devices of the present type, the combination of surfactant and a suitable membrane should yield a monomer transport curve wherein $S_1$ is relatively large, $S_2$ is relatively small, and $C_2$ is about equal to the cmc of the surfactant being tested. The ratio of $S_2/S_1$ is from 0 to about 0.1. $S_1$ should generally be no less than about 10 ppm/hr. and preferably will be in the range of about 100 ppm/hr. to about 200 ppm/hr.

Based on the foregoing, surfactant/membrane combinations can be selected which will provide controlled release articles of the present type. A highly preferred article herein which is particularly useful as a vaginal contraceptive comprises from about a 5% to about a 50% (wt.) aqueous solution of $C_{10}EO_5$ enclosed within a polydimethylsiloxane membrane.

BEST MODE

The preferred externally rimless contraceptive devices herein which are especially adapted for use within the vaginal cavity, comprise: (1) a front face, said front face constituting a transport surface comprising a semipermeable membrane, said membrane describing at least a portion of the walls of one or more containers, said containers holding; (2) a spermicide comprising an aqueous solution of a micelle-forming spermicidal surfactant compound of a concentration at or above the critical micelle concentration of said surfactant compound; (3) a back affixed to said front face; and (4) a resilient material situated in the form of an internal rim adjacent to the internal perimeter of the front face, said internal rim comprising vaginal retaining means. As depicted in the Figures, the internal rim which constitutes the vaginal retaining means can comprise a thickened annular region of the front face, the back face, or both.

A preferred device has the transport surface extending substantially across the front face. While the device can be flat, it is preferably dome-shaped or dish-shaped, whereby the front face of the device can be positioned to substantially cap the cervical os.

The membrane which comprises the front face (transport surface) of the device is preferably a silicone polymer which is substantially free from color-forming curing agents. The membrane has a thickness in the range of from about 0.3 mm to about 0.8 mm; 0.4 mm is preferred.

The most preferred embodiment of the present devices for *high speed* manufacture comprises: an externally rimless, double-walled contraceptive device of a dish- or dome-shaped configuration suitable for capping or blocking the cervical os, the front face of said device comprising a flexible, non-porous, semi-permeable membrane transport surface having a thickness of about 0.4 mm, said front face having a substantially thicker region around its interior edge, projecting into the interior of the device to form an internal rim, the back of said device comprising resilient, flexible material having a thickness of about 1.0 mm, said front and back walls being joined to provide an internally rimmed container, said container holding an aqueous solution comprising from about 10% to about 50% by weight of $C_{10}EO_5$, $C_{10}EO_6$, or mixtures thereof, said front face and said back both comprising a toxicologically acceptable silicone polymer substantially free from color forming curing agents.

EXAMPLE I

The following describes a typical method of manufacturing a device of the type depicted in the Figures herein.

Dow Corning® MDX 4-4210 Clean Grade Elastomer (Dow Corning Corporation, Midland, Mich.) is supplied in two parts: an elastomer base and a curing agent which, when mixed and cured, form the finished silicone polymer membrane transport surface. In practice, about 10 parts of elastomer base are mixed with about 1 part of curing agent. The mixture is deaerated in a vacuum chamber until no more entrapped air can be seen. The deaerated mixture is then injected into a mold cavity of appropriate dimensions for silicone membrane: the thickness of the front face of the device which comprises the transport surface membrane is ca. 0.35±0.15 mm. whereas the thickness of the back is ca. 1.00±0.15 mm. The base of the device has an outside diameter of ca. 55±10 mm. The height of the upper membrane of the double dome from the base of the device is ca. 20±5 mm, whereas the height of the lower membrane of the double dome from the base of the device is ca. 15±5 mm, whereby the total volume of the dome-shaped container resulting from sealing the edges of the device is ca. 5 cc. The silicone is cured by heating in the mold at ca. 125° C. for at least about 15 minutes.

The choice of curing agent for silicone polymers is not critical to the operation of the devices prepared in the manner of this invention. Depending on the particular silicone polymer chosen, various platinum-based, tin-based and peroxide-based catalysts or curing agents for silicones well known in the art are suitable for use in preparing silicone membranes. However, it has now been discovered that, in prolonged use in the vagina, some curing agents can cause the silicone membrane to become disclored. While this discoloration does not deleteriously affect the operation of the devices, they are rendered unsanitary in appearance. Apparently, some naturally-occurring sulfur and/or amino compounds present in vaginal fluids somehow interact with tin-based curing agents such as stannous octoate to cause the discoloration. Whatever the cause, it is preferable from an aesthetic standpoint, to avoid the use of tin-based curing agents and curing agents which form colored complexes with the components of vaginal fluids in the preparation of optimized articles of the present type. Accordingly, peroxide-based or, preferably, platinum-based silicone curing agents are preferred for use herein. Such materials are well known in the art and can be selected from listings in standard texts.

After having prepared the two halves of the double-walled device, a uniform layer of silicone adhesive (e.g., Silastic® Medical Adhesive Silicone Type A, Dow Corning Corporation) is placed around the periphery of the upper half of the device. The upper half and lower half are joined and pressed to squeeze out any excess adhesive from the seal area. The excess adhesive is removed and the adhesive which seals the device is allowed to cure for 24 hours, or longer.

An aqueous solution of the spermicidal surfactant is prepared. The solution is taken up in a syringe fitted with a 25 gauge needle. The surfactant solution is injected into the free space within the double dome-shaped device, through the thickened internal rim. With the needle still in place, any air remaining inside the device is removed. (Needle holes from this procedure do not leak with pressures encountered in use.)

After filling, the sealed device is placed in a retortable foil-plastic laminate pouch which is hermetically sealed. The pouch is placed in a retort at 30 psig for 30 minutes. After cooling, the retort is opened and the pouches are removed to provide individually packaged, sterile contraceptive devices suitable for distribution to users.

In use, the device is folded in half and placed in the vagina posterior to the introitus in a manner such that the transport surface substantially covers and "caps" the cervical os. The device opens automatically to cap the os, by virtue of the internal rim. The device is worn during the time between menses and safely and continuously delivers a spermicidally effective amount of $C_{10}EO_5$ surfactant directly to the cervical os. In particular, the positioning and shape of the device bathes the cervical os with the spermicidal surfactant and provides a mechanical barrier to motile sperm, further enhancing contraceptive efficacy. The device is quite comfortable and remains in place during intercourse.

Industrial Applicability

The following examples illustrate the practice of this invention, but are not intended to be limiting thereof. It is to be understood that the present invention also encompasses devices wherein the front (transport surface) face or the back provides the entire internal rim, at the option of the manufacturer. Devices of this "unit" construction can be manufactured in the manner and with the materials disclosed herein, but for hand manufacture, devices in which the thickened edges of each half are bonded to form the internal rim offer the manufacturing advantage of reinforced bonding surfaces on both halves of the unit.

EXAMPLE II

Figures 1, 2:
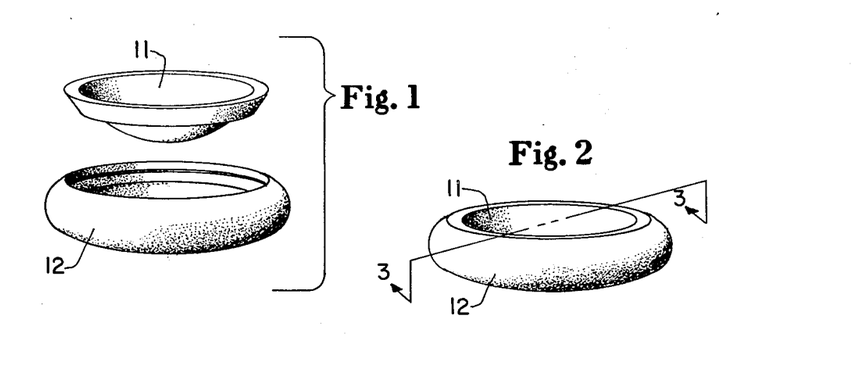
Figure 3:
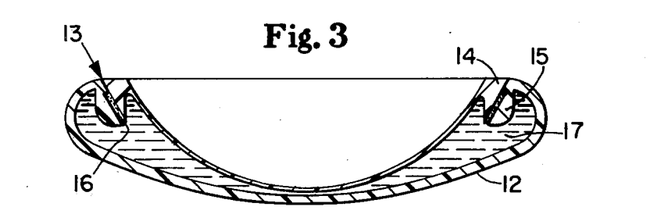
FIG. 3 is a section view of the assembled device through 3—3 showing the relationship of the front face which constitutes the transport surface for the spermicide, the back 12, the internal rim 13, formed by joining the thickened edge 14 of the front face, and the thickened edge 15 of the back, with an adhesive 16.
Figure 4:
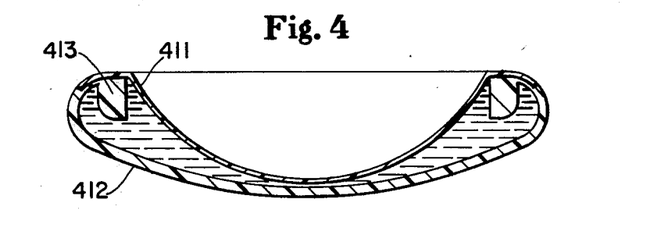
FIG. 4 depicts a cross section view of an alternative configuration for articles of the present invention, in which a thickened portion of the back half 412 of the device forms the entire internal rim 413.
Figure 5:
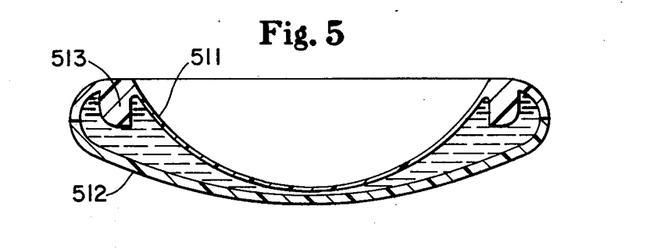
FIG. 5 depicts a cross section view of another alternative configuration for articles of the present invention in which a thickened portion of the front face 511 comprises the entire internal rim 513.

A device of the configuration depicted in FIG. 4 is prepared as follows. The internal portion of the device (i.e., the transport surface to be placed in close proximity to the cervical os) is prepared from Dow Corning ® MDX 4-4210 Clean Grade Elastomer using the methods described above. The thickness of the silicone membrane is ca. 0.25±0.15 mm.

The other half of the device is prepared from a substantially non-permeable, polyethylene (PE) plastic having a thickness of ca. 1.5±0.15 mm. An internal rim of the type depicted in FIG. 4 is cast into this half of the device.

The two halves are assembled in the manner described above to provide a disc-shaped device. The inner concavity of the device comprises the semi-permeable silicone membrane. The base of the device has an outside diameter of 55±10 mm, which is appropriate for the average user. The total volume of the device is ca. 5 cc.

A device of the foregoing type is substantially filled with a 25% (wt.) aqueous solution of the $C_{10}EO_5$ surfactant. Excess air is removed. The device is autoclaved and is ready for use as a vaginal contraceptive.

The device is folded and placed in the vagina posterior to the introitus in a manner such that the silicone membrane substantially covers the cervical os. The device is worn during the time between menses and safely and effectively delivers a spermicidal amount of $C_{10}EO_5$ surfactant to the vaginal area. In particular, the positioning and shape of the device bathes the cervical os with the spermicidal surfactant via the inner silicone membrane. Substantially none of the surfactant migrates through the PE outer dome into the general vaginal cavity. Thus, substantially all of the surfactant is delivered to the intended situs, i.e., the cervical os and immediate surrounding area. The device is quite comfortable and remains in place during ordinary muscular exertions.

EXAMPLE III

In the device of the foregoing Example, the $C_{10}EO_5$ surfactant is replaced by an equivalent amount of $C_{10}EO_6$ surfactant and excellent spermicidal results are secured.

EXAMPLE IV

The device of Example II is prepared using synthetic rubber and excellent spermicidal results are secured.

The device of Example II is prepared from the following polymeric materials: silicone/polycarbonate co-polymer; styrene/butadiene block copolymers; and ethylene-vinylacetate copolymers, said polymeric materials being used in combination with both $C_{10}EO_5$ and $C_{10}EO_6$. Excellent spermicidal results are secured.

What is claimed is:

1. An externally rimless contraceptive device especially adapted for use within the vaginal cavity, comprising:
   (a) a front face, said front face constituting a transport surface comprising a semi-permeable membrane, said membrane describing at least a portion of the walls of one or more containers, said containers holding;
   (b) a spermicide comprising an aqueous solution of a micelle-forming spermicidal surfactant compound of a concentration at or above the critical micelle concentration of said surfactant compound;
   (c) a back affixed to said front face; and
   (d) an internal rim, said internal rim comprising a resilient material adjacent to the internal perimeter of said front face.

2. A device according to claim 1 wherein the internal rim which constitutes the vaginal retaining means comprises a thickened region of said front face, said back, or both, in a substantially circular configuration.

3. A device according to claim 2 wherein the internal rim which comprises the vaginal retaining means is substantially entirely located on the back of the device.

4. A device according to claim 2 wherein the internal rim is formed by joining the thickened internal perimeter of both the front and back of the device.

5. A device according to claim 2 wherein the thickened internal rim which comprises the vaginal retaining means is substantially entirely located on the front face of the device.

6. A device according to claim 1 which is disc-shaped.

7. A device according to claim 6 wherein the transport surface extends substantially across the front face of the device.

8. A device according to claim 7 which is dome-shaped or dish-shaped, whereby the front face of the device can be positioned to substantially cap the cervical os.

9. A device according to claim 7 which is substantially flat, whereby the front face of the device can be positioned to substantially block the cervical os.

10. A device according to claim 1 wherein the semi-permeable membrane comprises a pharmaceutically-acceptable silicone polymer.

11. A device according to claim 10 wherein the silicone polymer is substantially free from color-forming curing agents.

12. A device according to claim 10 wherein the membrane has a thickness in the range of from about 0.02 mm to about 0.8 mm.

13. A device according to claim 1 wherein the spermicidal surfactant compound is a nonionic surfactant selected from ethylene oxide condensates of aliphatic alcohols and ethylene oxide condensates of alkyl phenols.

14. A device according to claim 13 wherein the surfactant compound is characterized by a critical micelle concentration of at most about $5 \times 10^{-3}$ Molar.

15. A device according to claim 14 wherein the surfactant compound is $C_{10}EO_5$, $C_{10}EO_6$, or mixtures thereof.

16. An externally rimless, double-walled contraceptive device according to claim 1 of a dome-shaped or dish-shaped configuration suitable for capping or blocking the cervical os, the front face of said device comprising a flexible non-porous, semi-permeable membrane transport surface having a thickness of about 0.4 mm, said front face having a substantially thicker region around its interior edge, projecting into the interior of the device to form an internal rim, the back of said device comprising resilient, flexible material having a thickness of about 1.0 mm, said front face and back being joined to provide an internally rimmed container, said container holding an aqueous solution comprising from about 10% to about 50% by weight of $C_{10}EO_5$, $C_{10}EO_6$, or mixtures thereof, said front face and said back both comprising a toxicologically acceptable silicone polymer substantially free from color forming curing agents.

17. A method for achieving contraception in the vagina, comprising: inserting within the vaginal cavity at a position posterior to the introitus and in close proximity to the cervical os a device according to claims 1 or 16 and placing the device so that the transport surface substantially caps or blocks the cervical os, wherein surfactant monomers diffuse from the device and substantially bathe the cervical os to provide a spermicidal effect.

* * * * *